United States Patent [19]

Clemow et al.

[11] Patent Number: 4,858,603
[45] Date of Patent: Aug. 22, 1989

[54] BONE PIN

[75] Inventors: Alastair J. T. Clemow, Princeton; Scott H. Jaeger, Cherry Hill, both of N.J.

[73] Assignee: Johnson & Johnson Orthopaedics, Inc., New Brunswick, N.J.

[21] Appl. No.: 202,602

[22] Filed: Jun. 6, 1988

[51] Int. Cl.⁴ .............................................. A61F 5/04
[52] U.S. Cl. ........................... 128/92 ZW; 128/92 YR
[58] Field of Search ........ 128/92 YQ, 92 YK, 92 YZ, 128/92 YV, 92 ZW, 92 Y, 92 YW, 92 YT, 92 YR, 92 YE, 335.5, 92 YN

[56] References Cited

U.S. PATENT DOCUMENTS

| 2,121,193 | 6/1938 | Haniche | 128/92 YV |
| 2,772,676 | 12/1956 | Pohl | 128/92 YV |
| 3,915,162 | 10/1975 | Miller | 128/92 YE |
| 4,052,988 | 10/1977 | Doddi et al. | 128/92 YQ |
| 4,414,966 | 11/1983 | Stednitz | 128/92 YE |
| 4,463,753 | 8/1984 | Gustilo | 128/92 YE |
| 4,628,923 | 12/1986 | Medoff | 128/92 YV |
| 4,756,307 | 7/1988 | Cronninshield | 128/92 YZ |

Primary Examiner—Robert A. Hafer
Assistant Examiner—Michael Brown

[57] ABSTRACT

A bone pin made with a tapered polymeric portion and a cutting device secured to the smaller end of the polymeric portion. The pin can be inserted through a bone or bone fragment and the cutting device removed.

5 Claims, 1 Drawing Sheet

BONE PIN

BACKGROUND OF THE INVENTION

The present invention relates to a bone pin which is used to secure small bone fragments together and which is made from a polymeric material, preferably a polymer which is absorbable in an animal body. The bone pin of the present invention has a cutting or drilling device secured to one end of the polymeric portion of the pin so that the pin may be directly inserted into a bone or a bone fragment.

Bone pins are generally made from a medical grade metal which can be placed in an animal body for extended periods of time without adverse effect. The metal bone pins are normally removed from the body after the bone has healed. The metal bone pins, particularly a bone pining device called a Kirschner wire, may have a sharpened end which can be used as a drill point to drill the pin through the bone.

The use of plastic such as polyethylene as a bone pin has been suggested. Bone pins made from polymeric materials which are absorbable in the body has also been suggested. These bone pins can be made from polyglycolide or polylactide polymers or copolymers or glycolide and lactide or from poly-dioxanone or other absorbable polymers. A bone pin made from poly-dioxanone as disclosed in U.S. Pat. No. 4,052,988 has been commercially available for some time.

The poly-dioxanone bone pin is employed by drilling a hole through a bone fragment and into a solid bone or between or through two adjacent fragments of bone which are to be held together. After a hole of the proper diameter is drilled through the bone, the drill is removed and the poly-dioxanone pin is inserted through the hole and the portion of the pin extending beyond the bone surface is removed by cutting with a scalpel or other instrument.

The problem with this procedure is that when the initial hole is drilled through the bone the bone fragments are aligned, after the drill is removed in order to insert the pin, the fragments may become misaligned which causes difficulty in properly inserting the pin.

BRIEF SUMMARY OF THE PRESENT INVENTION

The present invention provides a polymeric bone pin with a drill point attached to the polymeric pin. The present invention is particularly useful in procedures where a pin will extend completely from one surface of a bone to the opposite surface. The bone pin of the present invention can be positioned using a hollow drill. The drill point of the pin is drilled through the bones to be joined together. The drill point will extend beyond or completely through the distal surface of the bone. The pin is then pushed through the bones and the polymeric portions of the pin and the drill point which extend beyond the bone surface are removed. This procedure using the bone pin of the present invention, completely eliminates the problem of misaligning bone fragments since the pin immediately follows the drill point through the bone.

BRIEF DESCRIPTION OF THE DRAWINGS

In present application

DETAILED DESCRIPTION OF THE INVENTION

Figure 1:
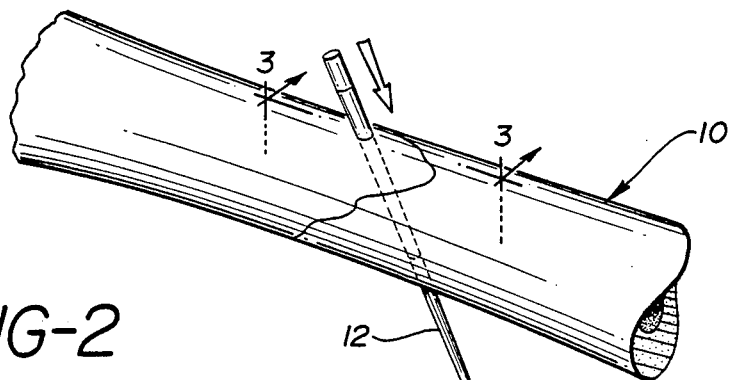
FIG. 1 shows two bone fragments being secured together by the pin being pushed through the fragments.
Figure 2:
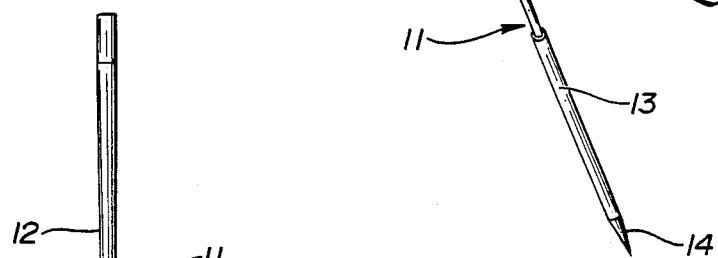
FIG. 2 shows the bone pin with the drill point attached.

FIG. 1 shows the use of the bone pin of the present invention. The pin is used to secure together portions of the bone 10. Pin 11 comprises a polymeric portion 12 with a drill portion 13 attached. The drill portion has a drill point 14 and is attached to the polymeric portion by swaging, with adhesive or by other methods.

The preferred nonabsorbent polymer used for the polymeric portion of the pin is polyethylene and the preferred absorbent polymer is the poly-dioxanone disclosed in U.S. Pat. No. 4,052,988.

The polymeric portion of the pin is tapered with a taper of from 0.005 to 0.05 millimeters per millimeter of length. The pin 11 generally would have a length between about 100 and 200 millimeters. The polymeric portion of the pin would have a length of approximately 50 to 100 millimeters and the cutting portion of the device would have a length of approximately 50 to 100 millimeters. The cutting device is affixed to that end of the polymeric portion of the pin with the smallest diameter. The polymeric portion of the device can be affixed to the cutting portion by swaging or with a connecting pin by cementing the two pieces together with epoxy or other suitable cement or a combination of these procedures. The cutting portion can be a piece of Kirschner wire with a hole drilled in the back of the wire to receive the absorbable portion of the device. The drilling point 14 of the cutting portion of the device is capable of drilling through bone when used with a hollow surgical drill. In using the hollow surgical drill, the cutting portion of the pin is held by the drill chuck and the polymeric portion of the pin extends into the body of the drill to the rear of the chuck. As shown in the drawing, the absorbable portion of the device has a taper of approximately 0.005 millimeter per millimeter of length to 0.05 millimeters per millimeter of length. The taper being the difference in diameter per mil of length. It should be noted that the cutting portion of the device has a diameter which is greater than the smallest diameter of the polymeric portion of the device but not as great as the largest diameter of the polymeric portion of the device. The taper of the pin allows the pin to be gradually forced into the hole that has been drilled through the bone. The pin diameter will eventually be as large or larger than the hole in the bone and can be force fit into the bone to secure the pin in the bone.

Figure 3:
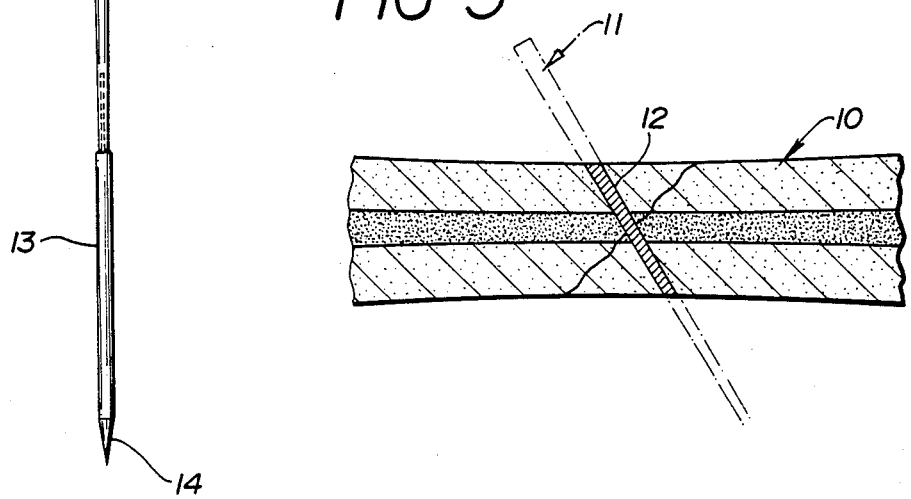
FIG. 3 shows the polymeric portion of the pin fixed in a bone.

After the pin is in place the portions of the pin extending beyond the bone as shown in FIG. 3 can be cut off with a scalpel or other suitable cutting device so that the pin is flush with the bone.

We claim:

1. A bone pin comprising a tapered cylindrical portion made of a polymeric material and a separate drill portion affixed to one end of the cylindrical polymeric portion, the cylindrical polymeric portion of the pin having a taper such that the diameter is reduced by from 0.005 to 0.05 millimeters per millimeter of length of the polymeric portion of the pin, the diameter of the drill portion being between the smallest diameter and the largest diameter of the polymeric portion.

2. The bone pin of claim 1 in which the polymeric portion of the pin is made from a polymer which is absorbable in an animal body.

3. The pin of claim 2 in which the polymeric portion of the pin is swaged to the drill portion of the device.

4. The bone pin of claim 2 in which the absorbable polymer is poly-dioxanone.

5. The pin of claim 1 in which the point of the drill portion is metal.

* * * * *